(12) United States Patent
Farooq et al.

(10) Patent No.: US 11,275,757 B2
(45) Date of Patent: Mar. 15, 2022

(54) SYSTEMS AND METHODS FOR CAPTURING DATA, CREATING BILLABLE INFORMATION AND OUTPUTTING BILLABLE INFORMATION

(71) Applicant: CERNER INNOVATION, INC., Kansas City, KS (US)

(72) Inventors: Faisal Farooq, Norristown, PA (US); Joseph Marcus Overhage, Zionville, IN (US)

(73) Assignee: CERNER INNOVATION, INC., North Kansas City, MO (US)

(*) Notice: Subject to any disclaimer, the term of this patent is extended or adjusted under 35 U.S.C. 154(b) by 893 days.

(21) Appl. No.: 15/043,098

(22) Filed: Feb. 12, 2016

(65) Prior Publication Data

US 2016/0239617 A1    Aug. 18, 2016

Related U.S. Application Data

(60) Provisional application No. 62/115,814, filed on Feb. 13, 2015.

(51) Int. Cl.
*G16H 10/60* (2018.01)
*G06F 16/25* (2019.01)
*G06Q 10/10* (2012.01)

(52) U.S. Cl.
CPC ......... *G06F 16/258* (2019.01); *G06Q 10/10* (2013.01); *G16H 10/60* (2018.01)

(58) Field of Classification Search
CPC .. A61N 1/3621; G06F 19/326; G06F 19/3456
See application file for complete search history.

(56) References Cited

U.S. PATENT DOCUMENTS 4,857,716 A    8/1989  Gombrich et al.
5,482,050 A    1/1996  Smokoff et al.
(Continued)

FOREIGN PATENT DOCUMENTS

DE    19844918 A1    4/2000

OTHER PUBLICATIONS

Tom Mooney. "Rhode Island ER first to test Google Glass on medical conditions", http://www.ems1.com/ems-products/cameras-video/articles/1860487-Rhode-Island-ER-first . . . Printed Mar. 11, 2014, 3 pages.
(Continued)

*Primary Examiner* — Reginald R Reyes
(74) *Attorney, Agent, or Firm* — Shook, Hardy & Bacon, L.L.P.

(57) ABSTRACT

Methods, systems, and computer-readable media are provided for generating and outputting medical billing data. Data is captured by pervasive devices before, during, and after a patient encounter with a healthcare provider. Any unstructured data is transformed into usable structured data, and determinations, such as a service provided by the healthcare provider, are made based on that data as well as other stored data. Based on those determinations, billing data for billing claims related to the patient visit is generated and outputted to a payer of the claims. The billing data may include a medical code that is predicted by a billing model. Billing models may be created from data captured by the pervasive devices from patient visits and data in external data stores, such as electronic health records.

4 Claims, 4 Drawing Sheets

(56) References Cited

U.S. PATENT DOCUMENTS

| | | |
|---|---|---|
| 5,786,850 A | 7/1998 | Pritchett et al. |
| 5,798,798 A | 8/1998 | Rector et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,804,656 B1 | 10/2004 | Rosenfeld et al. |
| 7,181,375 B2 | 2/2007 | Rao et al. |
| 7,323,991 B1 | 1/2008 | Eckert et al. |
| 7,612,679 B1 | 11/2009 | Fackler et al. |
| 7,617,078 B2 | 11/2009 | Rao et al. |
| 7,756,723 B2 | 7/2010 | Rosow et al. |
| 7,801,591 B1 | 9/2010 | Shusterman |
| 7,840,511 B2 | 11/2010 | Rosales et al. |
| 7,840,512 B2 | 11/2010 | Pandya et al. |
| 7,945,457 B2 | 5/2011 | Zaleski |
| 8,209,183 B1 | 6/2012 | Patel et al. |
| 8,237,558 B2 | 8/2012 | Seyed Momen et al. |
| 8,273,018 B1 | 9/2012 | Fackler et al. |
| 8,428,940 B2 | 4/2013 | Kristjansson et al. |
| 8,432,263 B2 | 4/2013 | Kunz |
| 8,565,500 B2 | 10/2013 | Neff |
| 8,612,211 B1 | 12/2013 | Shires et al. |
| 8,620,682 B2 | 12/2013 | Bechtel et al. |
| 8,831,957 B2 | 9/2014 | Taubman et al. |
| 8,868,436 B2 | 10/2014 | Gotthardt |
| 8,878,773 B1 | 11/2014 | Bozarth |
| 8,902,068 B2 | 12/2014 | Bechtel et al. |
| 8,953,886 B2 | 2/2015 | King et al. |
| 9,072,929 B1 | 7/2015 | Rush et al. |
| 9,129,506 B1 | 9/2015 | Kusens |
| 9,159,215 B1 | 10/2015 | Kusens |
| 9,257,120 B1 | 2/2016 | Alvarez Guevara et al. |
| 9,269,012 B2 | 2/2016 | Fotland |
| 9,292,089 B1 | 3/2016 | Sadek |
| 9,424,840 B1 | 3/2016 | Hart et al. |
| 9,420,227 B1 | 8/2016 | Shires et al. |
| 9,542,944 B2 | 1/2017 | Jablokov et al. |
| 9,563,955 B1 | 2/2017 | Kamarshi et al. |
| 9,601,115 B2 | 3/2017 | Chen et al. |
| 9,729,833 B1 | 8/2017 | Kusens |
| 9,792,914 B2 | 10/2017 | Alvarez Guevara et al. |
| 9,911,418 B2 | 3/2018 | Chi |
| 2002/0015034 A1 | 2/2002 | Malmborg |
| 2002/0077863 A1 | 6/2002 | Rutledge et al. |
| 2002/0082867 A1 | 6/2002 | MacCarter et al. |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0120133 A1 | 6/2003 | Rao et al. |
| 2003/0120134 A1 | 6/2003 | Rao et al. |
| 2003/0120458 A1 | 6/2003 | Rao et al. |
| 2003/0126101 A1 | 7/2003 | Rao et al. |
| 2003/0130871 A1 | 7/2003 | Rao et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0054760 A1 | 3/2004 | Ewing et al. |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0228245 A1 | 10/2005 | Quy |
| 2005/0249139 A1 | 11/2005 | Nesbit |
| 2006/0004606 A1 | 1/2006 | Wendl |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0206011 A1 | 9/2006 | Higgins et al. |
| 2006/0246921 A1 | 11/2006 | Russ |
| 2006/0259326 A1 | 11/2006 | Ambekar et al. |
| 2006/0279427 A1 | 12/2006 | Becker et al. |
| 2007/0033073 A1 | 2/2007 | Tajaliawal et al. |
| 2007/0156456 A1 | 7/2007 | McGillin et al. |
| 2007/0162304 A1 | 7/2007 | Rodgers |
| 2007/0180047 A1 | 8/2007 | Dong et al. |
| 2007/0183493 A1 | 8/2007 | Kimpe |
| 2007/0192133 A1 | 8/2007 | Morgan |
| 2007/0255348 A1 | 11/2007 | Holtzclaw |
| 2008/0004904 A1 | 1/2008 | Tran |
| 2008/0068447 A1 | 3/2008 | Mattila et al. |
| 2008/0123750 A1 | 5/2008 | Bronstein et al. |
| 2008/0125288 A1 | 5/2008 | Case |
| 2008/0147442 A1 | 6/2008 | Warner et al. |
| 2008/0201280 A1 | 8/2008 | Martin et al. |
| 2008/0204236 A1 | 8/2008 | Kraft-Oz |
| 2008/0221928 A1 | 9/2008 | Garcia et al. |
| 2008/0243896 A1 | 10/2008 | Sitomer et al. |
| 2008/0249376 A1 | 10/2008 | Zaleski |
| 2008/0249801 A1 | 10/2008 | Zaleski |
| 2008/0312961 A1 | 12/2008 | Alsafadi |
| 2009/0054735 A1 | 2/2009 | Higgins et al. |
| 2009/0062626 A1 | 3/2009 | Baldus et al. |
| 2009/0231124 A1 | 9/2009 | Klabunde et al. |
| 2010/0324936 A1 | 12/2010 | Vishnubhatla et al. |
| 2011/0093279 A1 | 4/2011 | Levine et al. |
| 2011/0206244 A1 | 8/2011 | Munoz-Bustamante |
| 2011/0225114 A1 | 9/2011 | Gotthardt |
| 2012/0159316 A1 | 6/2012 | Ash et al. |
| 2013/0054512 A1 | 2/2013 | Ephrat et al. |
| 2013/0138457 A1 | 5/2013 | Ragusa |
| 2013/0169781 A1 | 7/2013 | Hanina et al. |
| 2013/0222133 A1 | 8/2013 | Schultz et al. |
| 2014/0222462 A1 | 8/2014 | Shakil et al. |
| 2014/0297301 A1* | 10/2014 | Rock ..................... G16H 20/00 705/2 |
| 2014/0365242 A1 | 12/2014 | Neff |
| 2015/0025329 A1* | 1/2015 | Amarasingham ...... G16H 40/67 600/301 |
| 2016/0183864 A1 | 6/2016 | Kusens et al. |
| 2018/0012604 A1 | 1/2018 | Guevara et al. |
| 2018/0350144 A1* | 12/2018 | Rathod ................. A63F 13/216 |

OTHER PUBLICATIONS

"Intelligent Clinical Decision Support Systems Based on SNOMED CT," 32nd Annual International Conference of the IEEE EMBS, Buenos Aires, Argentina, Aug. 31-Sep. 4, 2010 by Ewelina Ciolko, BHSc, Fletcher Lu, PhD and Amerdeep Joshi, BSc, BHSc., 4 pages.

Non-Final Office Action dated Mar. 10, 2016 in U.S. Appl. No. 14/220,171, 21 pages.

Final Office Action received for U.S. Appl. No. 14/220,171, dated Apr. 13, 2017, 67 pages.

Final Office Action received for U.S. Appl. No. 14/220,171, dated May 3, 2018, 53 pages.

Non-Final Office Action received for U.S. Appl. No. 14/220,171, dated Nov. 3, 2016, 50 pages.

Non-Final Office Action received for U.S. Appl. No. 14/220,171, dated Aug. 22, 2017, 50 pages.

Non-Final Office Action received for U.S. Appl. No. 12/062,631, dated Aug. 5, 2016, 17 pages.

"SNOMED CT", International Health Terminology Standards Development Organization, Jan. 19, 2012, 1 page.

Weglarz, Geoffrey, "Two Worlds of Data—Unstructured and Structured", DM Review, Sep. 2004, pp. 1-5.

Non-Final Office Action received for U.S. Appl. No. 14/220,171, dated Jan. 14, 2019, 45 pages.

Final Office Action received for U.S. Appl. No. 14/220,171, dated Aug. 2, 2019, 46 pages.

\* cited by examiner

SYSTEMS AND METHODS FOR CAPTURING DATA, CREATING BILLABLE INFORMATION AND OUTPUTTING BILLABLE INFORMATION

CROSS-REFERENCE TO RELATED APPLICATIONS

This application claims priority to U.S. Provisional Application No. 62/115,814, entitled "Systems and Methods for Capturing Medical-Related Data, Creating Medical Billable Information and Outputting Medical Billable Information," filed Feb. 13, 2015, the disclosure of which is incorporated by reference in its entirety. This application is also related by subject matter to U.S. application Ser. No. 14/220,171 entitled "Integration of Multiple Input Data Streams to Create Structured Data," filed Mar. 20, 2014, the disclosure of which is incorporated by reference in its entirety.

TECHNICAL FIELD

The present disclosure generally relates to systems and methods for generating billing claims and information related thereto, by using at least one pervasive device capturing activities of a healthcare provider.

BACKGROUND

It is often more beneficial to have data in a structured and possibly coded format within electronic health records (EHRs). Structured clinical data captured from healthcare providers is critical to fully realize the potential of health information technology systems. This is largely because structured clinical data can be manipulated, read, understood, and analyzed more easily than unstructured data. Further, medical records that are not organized and complete can lead to frustration and, possibly, misinformation.

Current methods for capturing and/or creating structured clinical data require significant effort and time with associated costs. Such methods include direct manual entry of information into structured data fields in a document, such as a table or a form. Manual entry is laborious and often impractical. Another current method is using dictation system in which a healthcare provider speaks into a dictation machine that outputs the text, often as free text, or a system in which unstructured data is converted to structured data using optical character recognition or mark sense forms. Yet another method is to use keyword and template based documentation systems that try to optimize between structured inputs and freeform entry. Historically, these methods have not proven to be extremely effective and result in limited user satisfaction.

Having correct and updated data derived from a patient visit is essential for several reasons, including being able to provide an efficient and effective billing system. Currently, various medical codes, such as Current Procedural Terminology (CPT) codes, are used in billing systems. The CPT code set is a medical code set maintained by the American Medical Association that describes medical, surgical, and diagnostic services and is designed to communicate uniform information about medical services and procedures among physicians, coders, patients, accreditation organizations, and payers. CPT coding identifies services provided and is used by insurers to determine the amount of reimbursement that a practitioner will receive when he or she performs that service. Current methods for capturing and/or creating information needed for billing purposes, including CPT codes, generally requires converting unstructured data into structure data, which, as previously mentioned, traditionally requires significant effort and time with associated costs.

Even where unstructured data can quickly and accurately be converted to structured data, there are inefficiencies in obtaining the unstructured and structured data in the first place. For example, before, during or after an examination or other interaction between a healthcare provider and a patient, the healthcare provider may need to manually type or otherwise enter data into a database. Or, the provider may need to dictate notes into a dictation machine, which creates free-text output that must be converted into structured data. Also adding to the time-consuming nature of this process are documentation guidelines implemented by payers. Though the goal of these guidelines is to ensure appropriate payment for services and avoid fraud and abuse, following them may add additional steps in the recording process. These additional steps to create and/or record structured and unstructured data for the patient record require extra time and effort by the healthcare provider and his or her staff. For example, providers are seeing fewer patients and spending more time to adhere to documentation guidelines from payers. There is currently no system for automated monitoring of healthcare provider-patient interactions and generation of structured data for billing claims.

BRIEF SUMMARY

This summary is provided to introduce a selection of concepts in a simplified form that are further described below in the detailed description section. This summary is not intended to identify key features or essential features of the claimed subject matter, nor is it intended to be used as an aid in determining the scope of the claimed subject matter. The present invention is defined by the claims.

In brief and at high level, this disclosure describes, among other things, methods, systems, and computer-readable media for generating and outputting data for one or more billing claims using multiple data streams. These methods and systems acquire input data from various sources, including a patient's EHR and pervasive devices capturing data relating to a patient's visit with a healthcare provider. As used throughout this disclosure, "pervasive devices" is meant to generally refer to devices capable of acquiring and communicating information unobtrusively, substantially continuously, and in real time. Such pervasive devices may provide video, audio, text, or image data and may relate to an interaction between a patient and healthcare provider.

The input data received from the pervasive devices may include unstructured data and structured data. Where data is unstructured, the methods and systems further include transforming unstructured data received into structured data. The structured data, whether received directly from the pervasive device or transformed from unstructured data, is used to make determinations, including a determination of a service provided by the healthcare provider. Based on the determinations, billing data for one or more billing claims relating to the patient's visit is generated and output to a payer of the billing claims. Such billing data may include medical codes, such as CPT codes, and a list of possible issues related to billing.

A further embodiment of the present invention includes receiving unstructured data relating to a first patient visit from one or more pervasive devices and translating that data into structured data. Additionally, an indication or input of the medical codes corresponding to the first patient data is received. The medical codes and the structured data corresponding to the first patient visit are then used to create billing models for future visits. After unstructured data relating to a second patient visit is acquired and transformed into structured data, the billing models may be used in conjunction with at least the structured data to generate billing data for one or more billing claims related to the second patient visit. The billing models may, among other things, provide appropriate medical codes for services performed during the second patient visit. The generated billing data may then be output to a payer of the billing claims.

BRIEF DESCRIPTION OF THE DRAWINGS

Embodiments of the invention are described in detail below with reference to the attached figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used in this description to connote different elements of methods employed, the terms should not be interpreted as implying any particular order among or between various steps disclosed unless and except when the order of individual steps is explicitly described.

The present invention serves to facilitate temporal integration of multiple data streams (e.g., data arising from physical interaction between a healthcare provider and a patient). It may then generate structured clinical data based on inferences derived from such temporal integration. The techniques used by the present invention are minimally invasive and results in the healthcare provider spending more effort in providing patient care (e.g., examination, diagnoses, treatment, etc.) than documenting the process. Further, the present invention aids in the billing process by generating data for billing claims from the data captured from an interaction between a patient and a healthcare provider.

Accordingly, in one aspect, the present invention is directed to a method of generating and outputting data for one or more billing claims using multiple data streams. The method includes acquiring input data from one or more pervasive devices. The input data is related to a patient's visit with a healthcare provider. Based on the input data, one or more determinations are made. At least one determination may be a service provided by the healthcare provider. Then, based on the one or more determinations, billing data for one or more billing claims relating to the patient's visit is generated. Finally, the billing data is output to a payer of the one or more billing claims.

In another aspect, the present invention is directed to a method of generating data for one or more billing claims using multiple data streams and billing models. This method includes receiving unstructured input data for a first patient visit from one or more pervasive devices. The unstructured input data is related to the first patient visit. The unstructured input data is then transformed into structured data. An indication of a medical code associated with the first patient visit in also received. One or more billing models are created based on at least the received indication of a medical code and the structured data from the first patient visit.

The method further comprises receiving unstructured data for a second patient visit from the one or more pervasive devices and transforming this unstructured data into structured data. Based on the structured data and the billing models created, billing data for billing claims arising from the second patient visit is generated. This billing data may include a medical code associated with the second patient visit.

In a further aspect, the invention is directed to a system for generating and outputting data for billing claims. The system includes one or more pervasive devices for capturing data regarding the performance of a task related to a first patient visit with a healthcare provider and one or more data stores, which include at least an electronic heath record for a patient present at the first patient visit. The system further includes a non-transitory computer-readable medium for storing computer-executable instructions and a processor in communication with the one or more pervasive devices, the one or more data stores, and the non-transitory computer-readable medium. The processor is operative with the computer-executable instructions to acquire the unstructured input data from the one or more pervasive devices and transform the unstructured input data into structured data. Based on the structured data, the processor makes one or more determinations, including a service provided by the healthcare provider. Then, based on the one or more determinations, billing data for one or more billing claims relating to the first patient visit is generated and output to a payer of the one or more billing claims.

Figure 1:
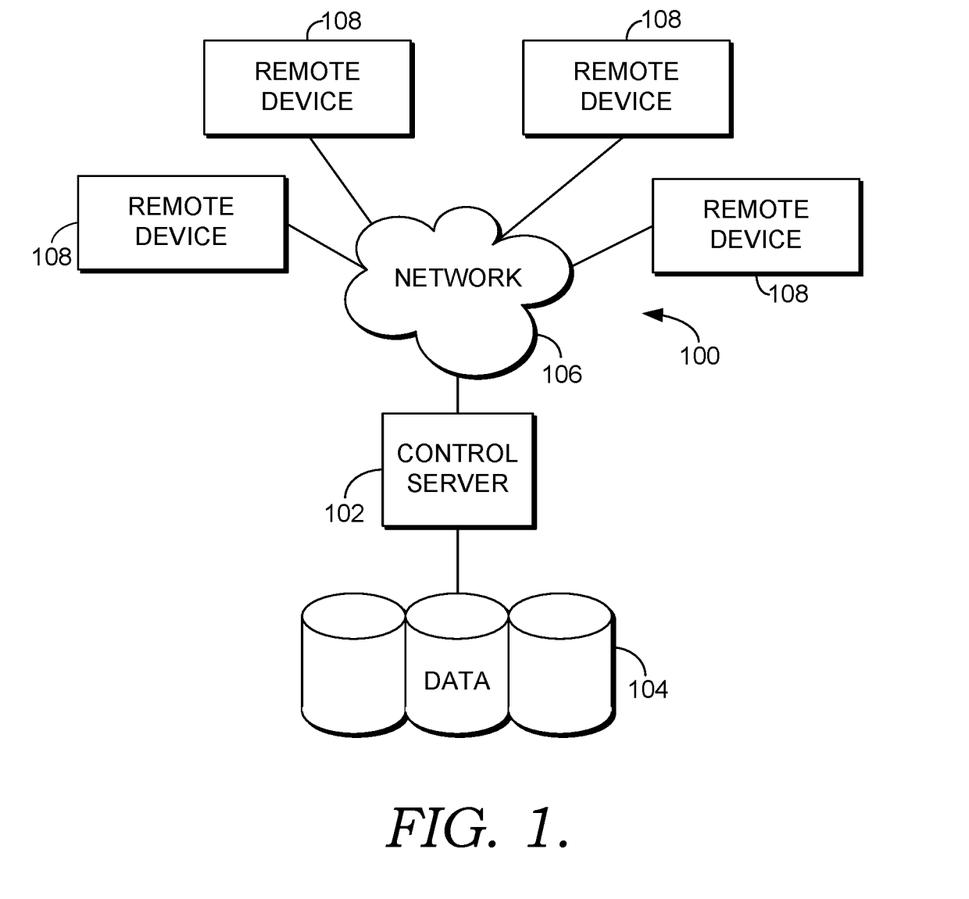
FIG. 1 is a block diagram of an exemplary computing environment suitable to implement embodiments of the present invention.

It is to be understood that the present invention may be implemented in various forms of hardware, software, firmware, special purpose processors, or a combination thereof. Preferably, the present invention is implemented in software as a program tangibly embodied on a program storage device. FIG. 1 shows an exemplary computing environment (e.g., medical-information computing system environment) for implementing embodiments of the system and method of the present disclosure. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a server 102. Exemplary components of the control server 102 comprise a central processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus. The computing environment 100 might also include a cache, a power supply, and clock circuits.

The control server 102 typically includes, or has access to, a variety of computer-readable media. Computer-readable media can be any available media that might be accessed by control server 102, and includes volatile and nonvolatile media, as well as, removable and non-removable media. By way of example, and not limitation, computer-readable media may comprise media implemented in any method or technology for storing information, including computer-storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote devices 108. Remote devices 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote devices 108 might also be physically located in nontraditional medical care environments so that the entire healthcare community might be capable of integration on the network. The remote devices 108 might be personal computers, servers, routers, network PCs, peer devices, other common network nodes, or the like and might comprise some or all of the elements described above in relation to the control server 102. The devices can be personal digital assistants or other like devices. Further, the remote devices 108 may include pervasive devices.

Computer network 106 may be any type of communication scheme that allows data exchange between devices. The computer networks 106 may include fiber optic, wired, and/or wireless communication capabilities in any of a plurality of protocols, such as TCP/IP, Ethernet, WAP, IEEE 802.11, or any other protocols. Implementations are contemplated in which the components of the computing environment 100 may be accessible through a shared public infrastructure (e.g., Internet), an extranet, an intranet, a virtual private network ("VPN"), a local area network (LAN), a wide area network (WAN), a peer-to-peer (P2P) network, a wireless communications network, telephone network, facsimile network, cloud network or any combination thereof.

In operation, an organization might enter commands and information into the control server 102 or convey the commands and information to the control server 102 via one or more of the remote devices 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote devices 108 might comprise other peripheral output devices, such as a monitor, speakers, and a printer.

Although many other internal components of the control server 102 and the remote devices 108 are not shown, such components and their interconnection are well known. Accordingly, additional details concerning the internal construction of the control server 102 and the remote devices 108 are not further disclosed herein.

Figure 2:
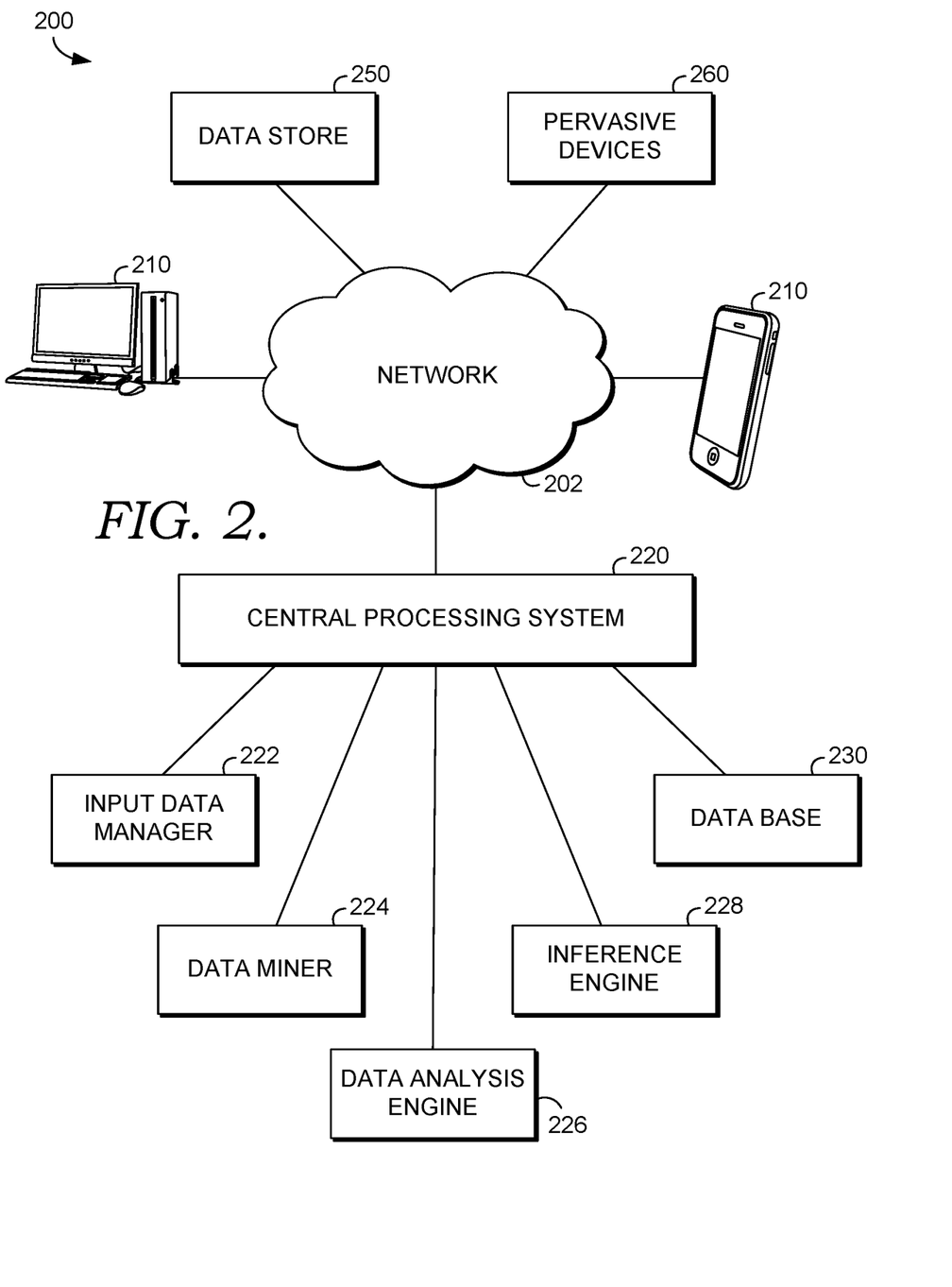
FIG. 2 is a black diagram of an exemplary system for generating and outputting billing data from multiple data streams, in accordance with embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 may include a display device (e.g. a dashboard, computer, mobile device, and the like), a central processing system 220, a data store 250, and one or more pervasive devices 260 all in communication with one another via a network 202. The network 202 may include, without limitation, one or more secure local area networks (LANs) or wide area networks (WANs). The network 202 may be a secure network associated with a facility, such as a healthcare facility, and may require a user to log in and be authenticated in order to send and/or receive information over the network 202.

The central processing system 220 may automatically assimilate medical information generated during the performance of a regular healthcare task (e.g., examination) without requiring additional effort on the part of the healthcare provider to record the information. In other words, the healthcare provider can provide normal and appropriate care with minimal extra effort in recording the medical data. The central processing system 220 achieves this by receiving or acquiring data from the pervasive devices 260 and the data store 250 and translates and analyzes the data to create output, such as output for billing claims. In some implementations, the central processing system 220 automatically and continuously captures the relevant information during, between, and after a patient encounter. In other words, the system 220 captures all relevant data generated during the healthcare provider's normal performance in examining, diagnosing, and/or treating a patient.

The central processing system 220 uses various components illustrated in FIG. 2. One or more of the illustrated components may be implemented as stand-alone applications in some embodiments. In other embodiments, one or more of the components may be distributed across multiple engines and/or may be located on any number of servers. As shown in FIG. 2, exemplary components of the central processing system 220 may include an input data manager 222, a data miner 224, a data analysis engine 226, an inference engine 228, and a database 230.

The database 230 may include a domain knowledge base. Information stored in the domain knowledge base may be provided as, for example, encoded input to the central process system 220, or by programs that produce information that can be understood by the system 220. The domain knowledge base may include, for example, domain-specific criteria that facilitate the assimilation of data (e.g., mining, interpreting, structuring, etc.) from various data sources (e.g., unstructured sources). Domain-specific criteria may include organization-specific domain knowledge. For example, such criteria may include information about the data available at a particular hospital, document structures at the hospital, policies and/or guidelines of the hospital, and so forth. Domain-specific criteria may also include disease-specific domain knowledge. For example, the disease-specific domain knowledge may include various factors that influence risk of a disease, disease progression information, complications information, outcomes and variables related to a disease, measurements related to a disease, policies and guidelines established by medical bodies, etc.

In exemplary embodiments, the central processing system 220 is communicatively coupled to multiple pervasive (or ubiquitous) devices 260. As used through this description, "pervasive devices" 260 generally refer to those devices that "exist everywhere" and are completely connected and capable of acquiring and communicating information unobtrusively, substantially continuously, and in real-time. Input data, or data received from the pervasive devices 260 within a defined geographic region (e.g., patient examination room, healthcare facility, etc.), can be acquired, monitored, and analyzed by the central processing system 220 to translate into structured data.

Data from the pervasive devices 260 can be used to make substantially real-time inferences regarding a patient's visit. For instance, data from various video sources can indicate duration of a face-to-face interaction between a patient and a healthcare provider, a duration of physical contact between a healthcare provider an a particular body region of the patient, and any interruptions during the interaction. Further, such data can provide a biometric signature or authentication of the healthcare provider and/or the patient, as well as patient movement parameters. Additionally, audio data from pervasive devices 260 may indicate a volume of dialog between the healthcare provider and the patient, an interaction index, and the tone and mood or sentiment of the patient. Further, patient vitals and patient's health condition may also be captured by pervasive devices 260.

The pervasive devices 260 may include unstructured or semi-structured data sources as well as structured data sources. The data from the pervasive devices 260 may include images, waveforms, textual documents, video files, audio files, position sensor data, motion sensor data, or measurement data. The data may be acquired by the central processing system 220 as a data stream or may be acquired as discrete data packets. In some implementations, multiple pervasive devices 260 are provided for collecting medical data during the examination, diagnosis, and/or treatment of a patient.

An exemplary pervasive device 260 includes a motion sensor that recognizes specific gestures, such as hand motions. Various methods may be used to track the movement of humans and objects in three-dimensional (3D) space. In one example, the motion sensor includes an infrared laser projector combined with a monochrome complementary metal-oxide-semiconductor (CMOS) sensor, which captures video data in 3D space under ambient light conditions. The sensing range of the instrument may be adjustable. The instrument may be strategically positioned in, for instance, the healthcare provider's office so that it can capture every relevant aspect of a patient examination. This may include, for example, capturing the healthcare provider's movements and/or positioning, as well as the patient's movement and/or positioning. Other pervasive devices 260 may include, but are not limited to, microphones, cameras, facial recognition systems and devices, and voice recognition systems and devices.

Other exemplary pervasive devices 260 include instruments used by a healthcare provider during the course of examining, diagnosing and/or treating a patient. Such healthcare devices include, but are not limited to, audio recording devices, dictation devices, blood pressure monitors, heart rate monitors, medical instruments (e.g., endoscopes, otoscopes, anoscopes, sigmoidoscopes, rhinolaryngoscopes, laryngoscopes, colposcopes, gastroscopes, colonoscopies, etc.), and the like.

The pervasive devices 260 may be located in a single location, such as an examination room, to gather data relating to a patient examination. The pervasive devices 260 may also be in other locations within a healthcare facility gathering data directly relating to the interaction between the healthcare provider and the patient. Additionally, some of the pervasive devices 260 may be wearable and may be moved around the healthcare facility with the healthcare provider and/or patient wearing the device. Such wearable pervasive devices 260 may include a wearable sensor and display, such as a wearable computer integrated with a front facing video camera and an optical head mounted display (e.g., Google Glass). Unlike with other pervasive devices 260, like the motion sensor discussed above, wearable pervasive devices 260 are not confined to one particular location within a healthcare facility but can acquire data about a patient's visit as the patient and/or healthcare provider move within the facility. Central processing system 220 may serve to register the wearable sensor and display for use within the healthcare facility, handle communications with other systems, and provide the location of the wearable sensor and display within the facility via, for example, a global positioning system (GPS), radio frequency identification (RFID), or any other positioning systems.

The pervasive devices 260 may further include a monitoring system (such as camera, microphones, and a video screen) placed in a manner so that the patient may be able to view what is being monitored. The patient is then able to see what is being recorded, which may help the patient be more comfortable with being monitored and may allow the patient to help the devices pick up information (e.g., ensuring the patient can be seen and/or heard by a pervasive device 260).

It should be understood that the exemplary pervasive devices 260 mentioned above may include any necessary software to read and interpret data (e.g., images, movement, sound, etc.). These pervasive devices 260 may collect or acquire data from the healthcare provider and/or from the patient. For example, a dictation device or microphone may be strategically placed near, proximate, or adjacent to the patient's mouth and/or the healthcare provider's mouth so as to capture words and sounds of the healthcare provider and the patient. As these pervasive devices 260 capture information about a patient's visit, (e.g. an examination with a physician), the data is sent to the central processing system 220. The central processing system 220 may be receiving multiple streams of data from these devices at the same time.

Further, in some implementations, the central processing system 220 is communicatively coupled to one or more external data stores 250. The data stores 250 may include, for example, a repository of patient records. The patient records may also be locally stored on database 230. Patient records may be computer-based patient records (CPRs), electronic medical records (EMRs), electronic health records (EHRs), personal health records (PHRs), and the like. The data store 250 may be implemented on one or more additional computer systems or storage devices. For example, the data store 250 may include a data warehouse system residing on a separate computer system, a picture archiving and communication system (PACS), or any other now known or later developed hospital, medical institution, medical office, testing facility, pharmacy or other medical patient record storage system.

In addition to receiving data from the pervasive devices 260, the central processing system 220 may extract information from the patient records stored in the data store 250 to obtain more information regarding a patient's visit. For example, the central processing system 220 may obtain data from an EHR regarding any orders entered by the provider for the patient visit, test results, examination notes, data review time, patient demographics, appointment data, and a problem list.

Figure 3:
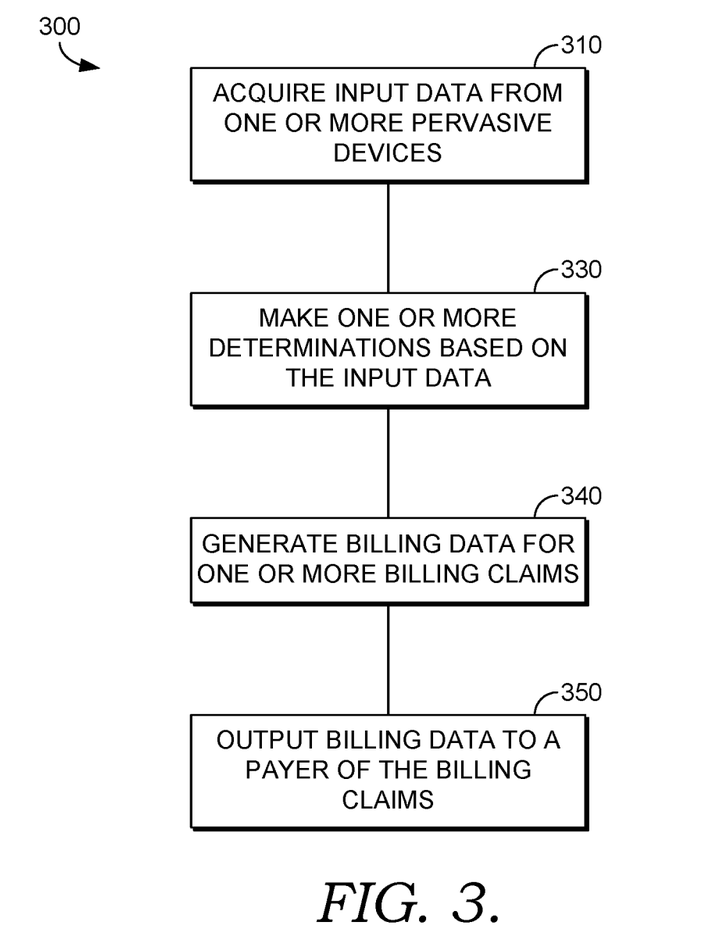
FIG. 3 is a flow diagram of an exemplary method for generating and outputting billing data from multiple data streams, in accordance with embodiments of the present invention.

FIG. 3 shows an exemplary method 300 of integrating multiple data streams for generating billing claims. The steps of the method 300 may be performed in the order shown or a different order. Additionally, different or fewer steps may be provided. Further, the method 300 may be implemented with the central processing system 220 of FIG. 2, a different system, or a combination thereof.

At 310, multiple input data streams are acquired by one or more pervasive devices 260. The data obtained may be related to a particular patient visit and more specifically, may be related to the performance of a regular task performed before, during, or after a healthcare provider's interaction with a patient. A "regular task" generally refers to a procedure that is undertaken during the normal course of business, and not for the sole purpose of recording structured data. In the context of a healthcare setting, exemplary regular tasks may be performed to examine, diagnose, and/or treat a patient. The pervasive devices 260 may be strategically placed on or near the patient and/or healthcare provider to automatically capture relevant data generated during the patient's encounter with the healthcare provider. The captured data may include, but is not limited to, 3D gestural input, speech recognition output followed by information extraction, image analysis, touch input, location awareness, biometric authentication (by, for example, ensemble methods), etc. The captured data may further include indications of time (e.g., time stamps) at which the data was acquired.

For example, the pervasive devices 260 may capture information from the healthcare provider, such as where his or her hand is placed with respect to the patient's body, where the healthcare provider is positioned relative to the patient, how the healthcare provider moves relative to the patient, and what the healthcare provider says to the patient, another provider, or any present third party. The pervasive devices 260 may also capture information from the patient, such as whether the patient's position (e.g., sitting, standing, bent over, laying down, etc.), what the patient says to the provider (e.g., symptoms, complaints, patient history, etc.), how the patient communicates (e.g., does the patient sound "hoarse" or is he or she having trouble speaking). The pervasive devices 260 may also capture notes taken by either the healthcare provider or the patient, where these notes may be hand-written, typed, coded, etc.

In exemplary embodiments, step 310 comprises acquiring multiple streams from multiple pervasive devices 260. For example, a healthcare provider may be equipped with a sensor capturing one or more images of the healthcare provider externally examining a portion of the patient's body. Additionally, a camera on a healthcare instrument, such as an endoscope, may be used to capture and send data regarding an internal examination of the patient. Lastly, a microphone may be present to obtain audio data from the examination.

Data from pervasive devices 260 may be structured data or unstructured data. In unstructured, the central processing system 220 must then transform the input data into structured data (e.g., results of tests, summaries of visits, symptoms etc.). In some embodiments, however, the input data is pre-processed by an input data manager 222 before being translated into structured data. The input data manager 222 pre-processes the captured input data streams to protect the privacy of the healthcare provider and/or the patient. For instance, the input data manger 222 may distort (e.g., make blur) or obscure the patient's face, voice, or any other identifying features. The input data manager 222 may also distort or remove personal information (e.g., the patient's name, social security number, birth date, account number, etc.). In some implementations, the input data manager 222 encodes the captured data before passing it on to prevent unauthorized persons from accessing it. In other aspects, processing may be performed by the pervasive device 260 itself. For example, a wearable sensor that takes video may perform video processing on the video files to parse out medical information for processing and storage as structured data before the data is sent to the central processing system 220.

The data analysis engine 226 automatically transforms the acquired data from the input data manager 222. The data analysis engine 226 may automatically translate unstructured or semi-structured data into a structured format. If the data is originally unstructured information (e.g., "free-text" output of a speech recognition system), it may be converted into structured data using various techniques, such as Natural Language Process (NLP), NLP using machine learning, NLP using neutral networks, image translation and processing, etc. Alternatively, if the data is already structured or suitable for structured format, it may be inserted into fields of a structured format.

In addition to the acquired input data, the data analysis engine 226 may also use mined data from a data miner 224. The data miner 224 collects relevant data from the data store 250. The data miner 224 may include an extraction component for mining information from electronic patient records retrieved from, for example, the data store 250. The data miner 224 may combine available evidence in a principled fashion over time, and draw inferences from the combination process. The mined information may be stored in a structured database (e.g., database 230), or communicated to other systems for subsequent use.

In some implementations, the extraction component employs domain-specific criteria to extract the information. The domain-specific criteria may be retrieved from, for example, database 230. In some implementations, the extraction component is configured to identify concepts in free text (e.g., a physician's treatment notes) using phrase extraction. Phrase extraction (or phrase spotting) may be performed by using a set of rules that specify phrases of interest and the inferences that can be drawn therefrom. Other natural language processing or natural language understanding methods may also be used instead of, or in conjunction with, phrase extraction to extract data from free text. For instance, heuristics and/or machine learning techniques may be employed to interpret unstructured data.

In some implementations, the extraction component employs a clinical ontology (e.g., Systematized Nomenclature of Medicine or SNOMED) to extract the information. The clinical ontology constrains the probable data options, which reduces the time and costs incurred in assimilating structured data. Use of clinical ontologies for mining and decision support is described in, for example, U.S. Pat. No. 7,840,512, which is incorporated by reference in its entirety herein. It describes a domain knowledge base being created from medical ontologies, such as a list of disease-associated terms.

Once data from the pervasive devices 260 or the data store 250 is translated into a structured format, it can be more easily manipulated, used, analyzed, and processed. At step 330, one or more determinations may be made based on the structured data. In some embodiments, the inference engine 228 makes one or more inferences regarding the patient's current state (e.g. the patient's diagnosis). Further, in regards to generating billing claims, the one or more determinations may include a service provided by the healthcare provider during the patient visit.

At step 340, the central processing system 220 generates billing data for one or more billing claims relating to the patient visit. The billing data may be generated from the one or more determinations made in step 330. Billing data may include medical codes, such as CPT, codes. In some embodiments of the invention, the CPT codes are automatically generated. In addition to CPT or other medical codes, generating billing data may further include verification of healthcare provider and patient identities. For example, biometric identification may be used to identify the healthcare provider and/or the patient based on data acquired from pervasive devices 260, such as height, facial configuration, etc. Though information relating to a patient's identity may be extracted from the external data store 250 (e.g., from an EHR), the central processing system 220 may apply "patient plagiarism monitoring" to confirm the person interacting with the healthcare provider is actually the patient listed in the electronic records. Additionally, the central processing system 220 can use the data to determine the healthcare provider was actually involved in the interaction and that different patients are being seen in different visit. Such monitoring would prevent a healthcare provider from having one person pretend to be a patient ten different times and billing the services as if the healthcare provider saw ten different patients. Any issues or problems relating to billing data, such as unverified patient identify or unidentified services, may be identified.

Finally, after the billing data is generated for the one or more billing claims, at step 350, the central processing system 220 outputs the billing data to a payer of the one or more billing claims. The payer may include an insurance company with a medical policy insuring the patient. Additionally, the billing data may be sent to the Centers for Medicare and Medicaid Services.

In other embodiments, medical codes are generated automatically only after the central process system 220 creates one or more billing models. This method 400 of generating billing claims is illustrated by the flow diagram in FIG. 4. First, at step 410, unstructured input data for a first patient visit is received from one or more pervasive devices 260, and at step 420, the unstructured input data is transformed into structured data for the first patient visit. Additionally, at step 430, an indication of one or more medical codes, such as CPT codes, relating to the first patient visit are received or extracted from a data store 250. These codes may have been manually entered into a patient's EHR by a healthcare provider. Other data may be received from the data store 250.

Figure 4:
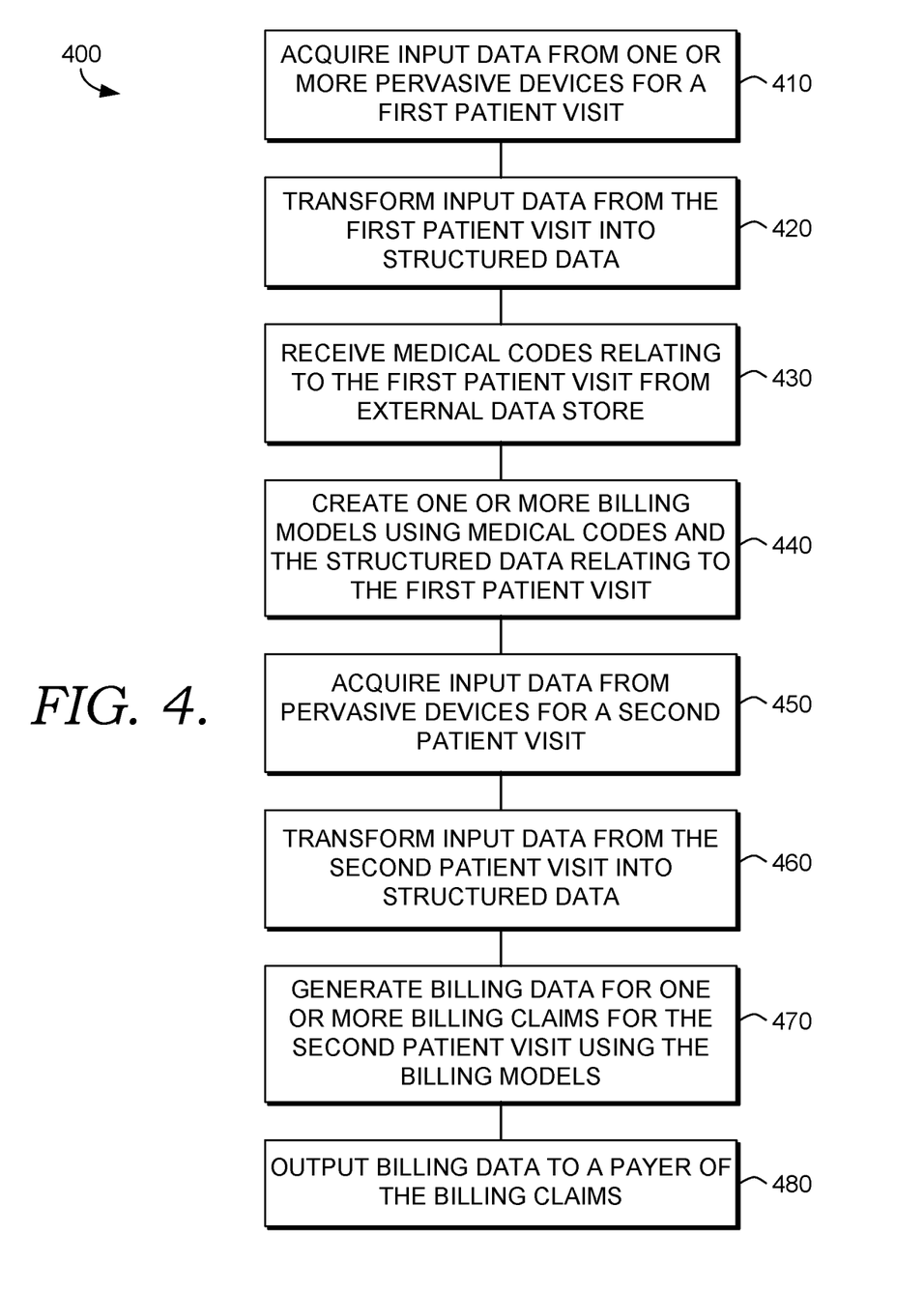
FIG. 4 is a flow diagram of an exemplary method for generating and outputting billing data from multiple data streams using billing models, in accordance with embodiments of the present invention.

At step 440, the central processing system 220 uses the CPT codes and the data from the pervasive devices 260 and the data store 250 to create the billing models. The codes received and the structured data from the pervasive devices 260 may be stored in association with each other. Further, the billing models may be based on hundreds or thousands of patient encounters with a healthcare provider such that the billing models learn from the stored associations between the received CPT codes and the data relating to patient visits, either from the pervasive devices 260 or the data store 250. In this manner, the central processing system 220 analyzes data streams from the pervasive devices 260 with selected data relating to a patient visit to compute a visit level from a billing model.

These billing models may be used for future patient visits. For example, at step 450, the method 400 includes acquiring unstructured input data from the one or more pervasive devices 260 for a second patient visit. At step 460, the unstructured patient data is transformed into structured data for the second patient visit. Then, at step 470, billing data is generated for one or more billing claims using the structured data for the second patient visit and the one or more billing models. In other words, the billing models eliminate the need for healthcare providers to manually enter CPT codes. The codes will be then be generated from the central processing system 220 based on the information captured during the visit from the pervasive devices 260 along with data from the data store 250. In some embodiments, the central processing system 220 may augment, by an NLP analysis of documentation, to get a lower level data that supports that CPT code. Finally, the billing data may also be output to a payer of the billing claims for the second patient visit, at step 480.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for generating and outputting data for billing claims using multiple data streams, the system comprising:
   a plurality of pervasive devices for automatically capturing unstructured input data in real time during an encounter between a patient and a healthcare provider during a patient visit, the unstructured input data comprising video data and audio data;
   one or more data stores, wherein the one or more data stores includes at least an electronic health record for the patient;
   a non-transitory computer-readable medium for storing computer-executable instructions; and
   a processor in communication with the plurality of pervasive devices, the one or more data stores, and the non-transitory computer-readable medium, the processor being operative with the computer-executable instructions to:
   acquire the unstructured input data from the plurality of pervasive devices;
   integrate the unstructured input data from the plurality of pervasive devices into structured data for the patient by encoding the unstructured input data from the plurality of pervasive devices using a clinical ontology;
   based on the structured data automatically captured from the plurality of pervasive devices, automatically determining one or more of a position of the healthcare provider relative to the patient during the encounter, movements of the healthcare provider relative to the patient, and a position of the patient's body during the encounter;
   based on the one or more determinations from the structured data captured from the plurality of pervasive devices, determine a service that is provided by the healthcare provider during the patient visit;
   based on the service determined to be provided by the healthcare provider, generate billing data for one or more billing claims relating to the patient visit; and
   outputting the billing data to a payer of the one or more billing claims.

2. The system of claim 1, wherein the processor includes an input data manager that pre-processes the unstructured input data captured by the plurality of pervasive devices to protect the privacy of the healthcare provider and/or the patient.

3. The system of claim 1, wherein the processor further receives input of one or more CPT codes for the patient visit.

4. The system of claim 3, wherein the processor stores the structured data and the one or more CPT codes and associates the structured data with the CPT codes.

* * * * *